United States Patent [19]

Gewartowski

[11] 4,410,754
[45] Oct. 18, 1983

[54] BUTYLENE ISOMERIZATION PROCESS

[75] Inventor: Steve A. Gewartowski, Mt. Prospect, Ill.

[73] Assignee: UOP Inc., Des Plaines, Ill.

[21] Appl. No.: 428,499

[22] Filed: Sep. 29, 1982

[51] Int. Cl.³ .......................... C07C 5/24; C07C 7/04
[52] U.S. Cl. ...................... 585/671; 203/82; 203/84; 585/332; 585/664; 585/802; 585/809
[58] Field of Search .............. 585/315, 316, 331, 332, 585/664, 665, 666, 667, 668, 670, 669, 671, 809, 802; 203/82, 84

[56] References Cited

U.S. PATENT DOCUMENTS

| | | | |
|---|---|---|---|
| 2,421,229 | 5/1947 | Zimmerman | 585/668 |
| 3,800,003 | 3/1974 | Sobel | 585/332 |
| 3,821,123 | 6/1974 | Germanas et al. | 260/439 |
| 4,104,321 | 8/1978 | Ward | 585/671 |
| 4,217,461 | 8/1980 | Ward | 585/671 |

FOREIGN PATENT DOCUMENTS

| | | | |
|---|---|---|---|
| 458135 | 7/1949 | United Kingdom | 585/667 |
| 407864 | 6/1970 | U.S.S.R. | 585/671 |

*Primary Examiner*—Delbert E. Gantz
*Assistant Examiner*—A. Pal
*Attorney, Agent, or Firm*—James R. Hoatson, Jr.; John F. Spears, Jr.; William H. Page, II

[57] ABSTRACT

An olefin isomerization process useful in recovering isobutylene from mixed butylene feed streams is disclosed. Preferably, the feed stream is passed through a first reaction zone to convert some butene-1 to butene-2 and then fed to the lower part of a two-part fractionation system. The butene-2-rich bottoms is withdrawn and the overhead vapor is passed through a second reaction zone in admixture with hydrogen before entering the second or upper part of the fractionation system. The bottoms liquid of the upper part of the fractionation system flows into the lower part of the fractionation system. Isobutylene and recycle hydrogen are recovered from the overhead vapor of the upper part of the fractionation system.

9 Claims, 1 Drawing Figure

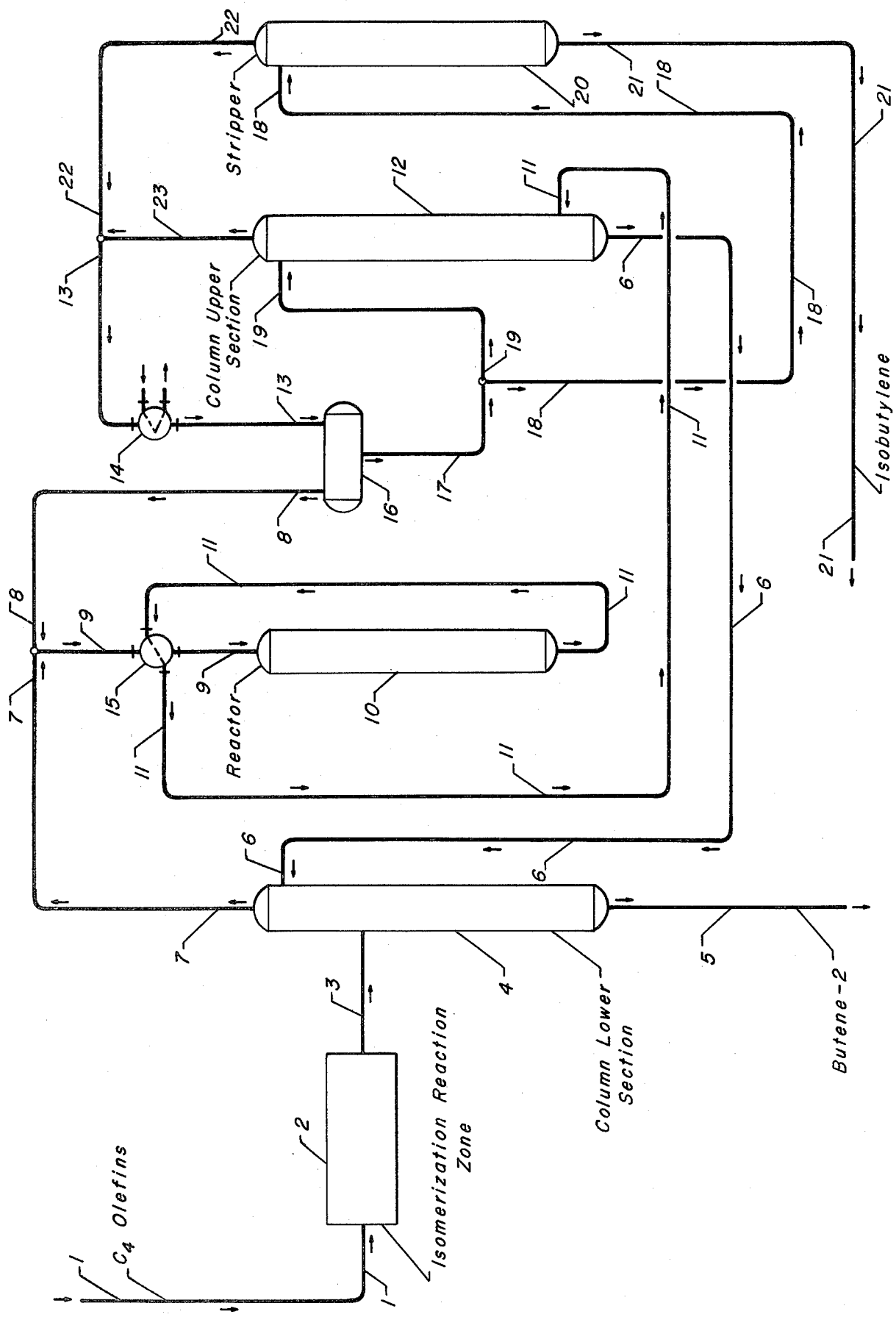

BUTYLENE ISOMERIZATION PROCESS

FIELD OF THE INVENTION

The invention relates in general to the processing of hydrocarbons as is performed in petroleum refineries and petrochemical plants. The invention more directly relates to a process for isomerizing light acyclic olefinic hydrocarbons. The invention is specifically directed to a process wherein isobutylene is recovered from a mixed butylene feed stream in an integrated process involving butene isomerization and fractionation.

PRIOR ART

The isomerization of normal olefinic hydrocarbons is described in U.S. Pat. No. 3,821,123. This reference describes a preferred catalyst for use in the isomerization of butene-1 to butene-2. The reference also discusses an isomerization process utilizing the catalyst and includes a description of the olefinic hydrocarbons which may be processed and suitable reaction conditions. U.S. Pat. No. 3,800,003 discloses a process wherein a feed stream comprising a mixture of different butylenes is combined with a recycle stream comprising butene-1 and isobutylene and is then passed into an isomerization reactor. The effluent of the isomerization reactor is passed into a fractionator which concentrates the product butene-2 into a bottoms stream.

U.S. Pat. No. 4,217,461 also presents a process for the isomerization of light olefinic hydrocarbons. This reference discloses the admixture of a feed stream comprising butene-1 with a recycle stream comprising hydrogen and a recycle stream comprising butene-2 and the passage of the resultant admixture into the first of two butene isomerization zones operated in series flow. The effluent of the second isomerization zone is passed into a vapor-liquid separation zone, with the hydrogen-containing recycle stream being withdrawn from this vapor-liquid separation zone. The hydrocarbon liquid stream removed from this separation zone is passed into a fractionation column and the overhead stream of this fractionation column is returned to the isomerization zone as the recycle stream which comprises butene-1.

U.S. Pat. No. 4,104,321 discloses a process for the separation of light olefinic hydrocarbons such as butylenes which utilizes two olefin isomerization reaction zones and a factionation column. The effluent stream of the first reaction zone is passed into the fractionation column. The overhead stream of the fractionation column is passed into the second reaction zone. In the preferred mode of this reference the bottoms product of the fractionation column is butene-2, but the isobutylene product stream is recovered directly from the effluent of the second reaction zone.

BRIEF SUMMARY OF THE INVENTION

The invention provides a novel process for the isomerization of light acyclic olefinic hydrocarbons which is especially useful in recovering pure streams of one or more of the olefins such as isobutylene. The novel process is distinguished from prior art processes by the use of a terminal reaction zone which receives as its feed stream the vapors passing upward through a two part fractionation system. The entire hydrogen-containing effluent of the reaction zone enters the remaining "upper" section of the fractionation system while liquid flowing "downward" from this section of the fractionation system bypasses the reaction zone and enters the lower section of the fractionation system. Novel hydrogen recirculation and heat exchange methods are also disclosed.

One embodiment of the invention may be broadly characterized as a process for the isomerization of acyclic olefinic hydrocarbons which comprises the steps of passing a feed stream comprising a first, a second and a third acyclic olefinic hydrocarbon, all of which have the same number of carbon atoms per molecule, through a first catalytic isomerization reaction zone and thereby producing a first reaction zone effluent stream which has a higher concentration of the first olefinic hydrocarbon than the feed stream; separating the first reaction zone effluent stream in a first fractionation zone into a first bottoms liquid stream having a higher concentration of the first olefinic hydrocarbon than the first reaction zone effluent stream and a first vapor stream having a higher concentration of the second olefinic hydrocarbon than the first reaction zone effluent stream and which is removed from an upper portion of the first fractionation zone; passing the first vapor stream through a second catalytic isomerization reaction zone and thereby producing a second reaction zone effluent stream which has a higher concentration of the first olefinic hydrocarbon than the first overhead vapor stream; separating the second reaction zone effluent stream in a second fractionation zone into a second bottoms liquid stream comprising the first olefinic hydrocarbon and a second vapor stream, which is rich in the third olefinic hydrocarbon; passing the second bottoms liquid stream into an upper portion of the first fractionation zone; and recovering a product stream which is rich in the third olefinic hydrocarbon from said second vapor stream.

DESCRIPTION OF THE DRAWING

The Drawing illustrates the preferred embodiment of the invention. However, this representation of one embodiment of the invention is not intended to thereby preclude from the scope of the inventive concept those other embodiments disclosed herein or which result from the reasonable and expected modification to those embodiments which may be made by those skilled in the art. For purposes of simplicity and ease of understanding, many pieces of apparatus which are normally employed in the operation of the process, such as pumps, compressors, process control equipment, reboilers, flow control valves, etc., have not been shown.

Referring now to the Drawing, a $C_4$ feed stream which comprises an admixture of butene-1, butene-2 and isobutylene and which preferably contains only minimal amounts of any saturate $C_4$ hydrocarbons is passed into an isomerization reaction zone 2 through line 1. In this reaction zone, the preferred configuration of which is described herein, the feed stream and hydrogen is contacted with an isomerization catalyst under conditions which affect the conversion of a significant quantity of butene-1 to butene-2. This produces a first reaction zone effluent stream carried by line 3 which has a higher butene-2 concentration than the feed stream. This liquid phase stream is passed into an intermediate point of a first fractionation zone 4 referred to as the column lower section and is therein separated into a first bottoms liquid stream having a very high concentration of butene-2, which is withdrawn through line 5 and a first overhead vapor stream withdrawn through line 7.

The overhead vapors removed from the column lower section 4 are combined with a hydrogen-containing recycle stream carried by line 8 and passed into line 9. The resultant admixture is then heated by indirect heat exchange against the effluent of the reactor 10 carried by line 11 in an indirect heat exchange means 15. The admixture is then preferably further heated in a second indirect heat exchange means not shown and passed into the reactor 10 which functions as the second reaction zone of the subject process. The entering hydrocarbons are therein contacted with an isomerization catalyst at conditions effective to convert an additional amount of the butene-1 to butene-2 and thereby produce a second reaction zone effluent stream having a higher butene-2 concentration than the stream entering the reactor 10. This second reaction zone effluent stream is cooled by passage through the heat exchange means 15 and is then passed into a lower section of a second fractionation zone referred to as the lower column section 12 as the feed stream and heat source to this section of the column. The compounds entering the upper section of the column are separated into a second bottoms liquid stream carried by line 6 which comprises the great majority of all the butene-2 entering the upper column section 4 and a second overhead vapor stream removed through line 23.

The second overhead vapor stream is admixed with a vapor stream carried by line 22 and passed through a partial condenser 14 via line 13. The resultant mixed phase stream is then passed into the overhead receiver 16. The hydrogen-containing recycle stream is withdrawn through line 8 to supply hydrogen to the reactor 10. A portion of the uncondensed gases present in the overhead receiver is removed as a light ends drag stream through a line not shown, and makeup high purity hydrogen is charged to the overall process also through a line not shown. A liquid which accumulates in the overhead receiver is withdrawn through line 17 and divided into a first portion which is returned to the uppermost portion of the upper column section through line 19 as a reflux stream and a second portion which is removed through line 18 and passed into a stripper column 20. The smaller stripper column 20 functions to strip hydrogen and light ends from the entering hydrocarbons to thereby produce a high purity stream of isobutylene which is removed through line 21 as a product of the process.

DETAILED DESCRIPTION

There is often an imbalance between the need of a certain olefin isomer used as a feedstock to a petroleum or petrochemical process and the available supply of that particular isomer. This may result when a particular olefinic isomer is used as the preferred feedstock to the process or when the olefin-consuming reaction is very specific and only one isomer is consumed or is preferentially consumed in the reaction of the process. For instance, it is normally desired to utilize butene-2 as the olefin feedstock in the HF-catalyzed alkylation process in which a $C_4$ olefin is reacted with isobutane to produce high octane number gasoline blending components since this results in a superior quality alkylate than the alkylation of butene-1. Another example is the etherification reaction between methanol and isobutylene, with this reaction being essentially totally selective for isobutylene despite the presence of other $C_4$ olefins. Yet another example is the desire to utilize specific olefins as the feedstock to oligomerization or polymerization reactions. Butene-2 is also consumed in the production of several chemicals which are widely used or are themselves consumed in other chemical products including various plastics and solvents. Some of the more widely used chemicals produced from butene-2 are sec-butyl alcohol, maleic anhydride, butadiene and methylethyl ketone. It is therefore often necessary to eliminate the imbalance between the need and the supply for a specific olefinic hydrocarbon by isomerization of available olefins into the desired olefin.

The utilization of specific olefin isomers is often also restricted by the difficulty of separating the isomers. The separation of isomers by the traditional technique of fractionation is a relatively expensive and difficult separation due to the close relative volatilities of the different isomers. It is therefore an objective of the subject invention to provide a process for isomerizing light olefinic hydrocarbons. It is another objective of the subject invention to provide a process for recovering a high purity stream of one olefinic isomer from a feed stream comprising three or more olefinic isomers. It is a specific objective of the invention to provide a process for recovering butene-2 and isobutylene from a feed stream comprising butene-1.

The feed stream to the subject process is preferably a mixture of butene-1, butene-2 and isobutylene which contains only a minor amount of saturate hydrocarbons or hydrocarbons having more than four carbon atoms per molecule. Such feed streams may be derived from thermal cracking processes used to produce ethylene or from the fluidized catalytic cracking process used to convert various gas oils or heavier hydrocarbons into gasoline and other fuels. The subject process is, however, not inherently limited to a butylene feedstock and may be applied with other light acyclic olefins if the presence of more than one isomer is acceptable in one or both of the product streams removed from the process. The process may therefore be generally applied to the isomerization of olefinic hydrocarbons having less than eight carbon atoms per molecule.

The subject process employs two separate and independent isomerization reaction zones. The feed stream to the process is charged directly into the first isomerization reaction zone. This reaction zone may contain a single reactor but preferably comprises two separate fixed bed reactors each of which contains a particulate isomerization catalyst. It is preferred that the first of these reactors is operated at a somewhat higher temperature. It is also preferred that the effluent of the second reactor is passed through an indirect heat exchange means which functions as a condenser and the resultant mixed phase stream is passed into a vapor-liquid separator. The uncondensed vapor is withdrawn from the separator and recirculated to the inlet of the first reactor as the recycle hydrogen stream and the condensate is withdrawn from the separator for passage into the downstream fractionation zone. Therefore the effluent stream of the first reaction zone preferably is a liquid phase stream comprising the various olefinic hydrocarbons and which contains no separate vapor phase stream and hence no hydrogen other than that dissolved in the liquid phase hydrocarbons.

The isomerization of light olefins is a quite mild reaction and available catalysts are highly stable. Facilities for the regeneration or replacement of catalyst are therefore not normally necessary. Within the isomerization zones, the entering reactants are contacted with the catalyst at isomerization conditions in a manner which effects a significant conversion of a feed olefinic hydrocarbon to a product olefinic hydrocarbon. A broad range of light olefin isomerization conditions includes a temperature of about 50° to about 250° C., a pressure of about atmospheric to 800 psig and a liquid hourly space velocity (LHSV) based on fresh feed of between 0.5 and 10.0. As the second isomerization zone and fractionation zones are at equivalent pressures, the pressure employed in the second isomerization zone is limited in part by the increased costs of building fractionation columns designed for high operating pressures. The molal hydrogen to hydrocarbon ratio maintained in the isomerization zones may range from about 0.02:1.0 to 1.0:1.0 or higher. A more preferred range of isomerization conditions includes an inlet temperature between about 85° and 170° C., a pressure between 50 and 300 psig and an LHSV between 1.0 and 5.0. The pressure within the second isomerization zone is preferably close to the pressure within the fractionation zones, with some pressure difference due to inherent pressure drops required to drive vapor flow being acceptable.

The isomerization reactors may be loaded with any commercially acceptable olefin isomerization catalyst of suitable activity and stability. Such catalysts are known to those skilled in the art and are available from catalyst manufacturing concerns. The preferred catalyst comprises a catalytically effective amount of a Group VIII metal and a solid porous refractory support, also referred to as a carrier material. The support material may be one of the aluminas, a zeolite or a similar material. The catalyst may be in the form of spheres, pellets or an extrudate and the metal component may be added in one of the known manners such as cogelation or impregnation onto formed support particles. An especially preferred catalyst is described in U.S. Pat. No. 3,821,123. This catalyst is produced by forming an initial composite comprising nickel and the support material, sulfiding the composite until it contains at least 0.9 mole of sulfur per mole of nickel and then stripping sulfur from the composite until it contains less than 0.55 mole of sulfur per mole of nickel. Further details on the preferred catalyst are provided in the patent.

The effluent of the first isomerization reaction zone is passed into a fractionation means which may be a single, unitary column instead of the two part column shown in the Drawing. In this unpreferred alternative, a vaporous sidecut is withdrawn as the feed to the second reaction zone. Preferably the effluent of the first isomerization reaction zone is passed into the lower section of the two-part fractionation column. Such two-part columns are occasionally employed when it is desired to limit the height of the fractionation column for either structural or operational convenience. The vapor stream which emanates from the lower section of the fractionation column is referred to herein as a first vapor stream or a first overhead vapor stream although it is not removed from the actual top of the fractionation column. The reference to this vapor stream as an overhead vapor stream is for the purpose of distinguishing this stream from other vapor phase streams which could be withdrawn from the lower section of the column such as sidecut streams. This vapor stream is passed through the second isomerization reaction zone and then into a bottom of the upper section of the fractionation column without intervening condensation or separation. That is, the total mass of vaporous hydrocarbons leaving the top of the lower section of the column is passed into the bottom of the upper section of the column. A liquid stream is withdrawn from the bottom of the upper section of the fractionation column and passed into the top of the bottom section of the fractionation column. Again, while this stream is referred to as a bottoms stream, it is not a true bottoms stream. However, this terminology serves to distinguish the stream from sidecut streams, etc., and is therefore felt to be the best available descriptive term.

The upper and lower sections of the fractionation column are referred to herein as the first and second fractionation zones, but function as a single fractionation column in which the vapor rising through an intermediate point in the column is caused to contact the isomerization catalyst of the second reaction zone. The effluent stream of the first reaction zone preferably enters the lower section of the fractionation column at an intermediate point which allows a substantial separation of the entering hydrocarbons into an overhead vapor stream and a bottoms liquid stream of substantially different compositions, with the bottoms liquid stream being rich in the least volatile isomer or class of isomers present in the feed. As used herein, the term "rich" is intended to indicate that the molar concentration of the specified chemical compound or class of compounds is greater than 50%.

The vapor stream removed from the top of the first fractionation zone is passed into a second catalytic isomerization reaction zone as a reactant stream. In the event a unitary fractionation column is utilized, this vapor stream is a sidecut stream, which may be achieved through partial or total blockage of the column to upward vapor flow. It is preferred that in the second reaction zone the reactant stream makes a single pass through a fixed bed reactor. The reactant stream comprises both the vapor stream removed from the lower section of the fractionation column (first fractionation zone) and a hydrogen-containing recycle stream. It is preferred that these two streams are first admixed and then heated by indirect heat exchange against that portion of the reactant stream which has already passed through the reactor. Additional heating by indirect heat exchange to bring the reactant stream up to the desired isomerization conditions is also preferred. The second reaction zone preferably contains the same catalyst as the first reaction zone. The effluent of the second reaction zone is preferably a vapor phase stream which contains all of the hydrogen charged to the reactor and hence is not subjected to the partial condensation and vapor-liquid separation steps employed in the first reaction zone. The effluent stream is preferably passed into the second fractionation zone (upper section of the column) as the only feed stream to this fractionation zone. It preferably enters immediately below the lowermost fractionation tray employed in this upper section of the column. The separatory action which occurs within this fractionation zone results in the concentration of an additional amount of the less volatile isomer or isomers into the liquid stream which is withdrawn and passed into the first fractionation zone. The less volatile isomers formed in the second isomerization reaction zone are therefore concentrated into this liquid stream and passed into the first fractionation zone for eventual removal as part of the bottoms product of the first fractionation zone.

The overhead vapor stream removed from the second fractionation zone preferably is passed through an overhead condensing means, which may be of conventional design, to produce a mixed phase stream which is passed into the overhead receiver. The vapors which accumulate in the overhead receiver are withdrawn, compressed, and divided into two smaller streams. One of these streams forms a vent gas stream which is continuously removed at a low rate to prevent the accumulation of various light ends within the process. The second of these two streams is recycled by admixture into the overhead vapor stream of the first fractionation zone as the previously referred to hydrogen-containing gas stream. The liquid phase material which accumulates in the overhead receiver is preferably divided into a reflux stream charged to the top tray of the second fractionation zone and a second stream which is passed into an optional product stripping column. The function of the relatively small product stripping column is to remove hydrogen and any light hydrocarbons from the product stream. The liquid withdrawn from the overhead receiver may therefore be removed from the process directly as a product stream if the presence of these more volatile compounds is acceptable.

A preferred embodiment of the invention may accordingly be characterized as a hydrogen conversion process which comprises the steps of passing a feed stream comprising butene-1, butene-2 and isobutylene through a first catalytic isomerization reaction zone maintained at isomerization conditions and in which butene-1 is converted to butene-2 and thereby producing a first reaction zone effluent stream, which comprises butene-1, butene-2 and isobutylene; separating the first reaction zone effluent stream in a first fractionation zone into a first bottoms liquid stream, which is rich in butene-2, and a first overhead vapor stream comprising butene-1 and isobutylene; admixing a recycle vapor stream comprising hydrogen into the first overhead vapor stream; passing the first overhead vapor stream into a second catalytic isomerization zone maintained at isomerization conditions in which butene-1 is converted to butene-2 and thereby producing a second reaction zone effluent stream, which comprises butene-1, butene-2, isobutylene and hydrogen; separating the second reaction zone in a second fractionation zone into a second bottoms liquid stream, which comprises butene-1 and butene-2, and a second overhead vapor stream, which comprises hydrogen and isobutylene; passing the second bottoms liquid stream into the first fractionation zone; and recovering a product stream comprising isobutylene from the second overhead vapor stream.

The process of the subject invention is further illustrated by the following example, which is based on the projected operation of a commercial scale process unit having a flow similar to that shown in the Drawing. The feed stream has a total flow rate of about 1340 mph (moles per hour) of which about 710 mph is isobutylene, 360 mph is butene-1 and 215 mph is butene-2. This feed stream is combined with a recycle gas stream containing about 670 mph of hydrogen and is then passed into the first of the two reactors utilized in the first reaction zone. The effluent of the first reactor is partially condensed to form a liquid stream and a vapor stream containing a large majority of the hydrocarbons and most of the hydrogen present in the effluent of the first reactor. The vapor phase is reheated and passed into the second reactor while the liquid stream is bypassed around the second reactor and admixed with condensate recovered from the effluent of the second reactor. The liquid stream produced as the effluent of the first isomerization reaction zone has a flow rate of approximately 1340 mph of which about 690 mph is isobutylene, about 65 mph is butene-1 and about 525 mph is butene-2. This effluent stream is passed into an intermediate point of a lower section of a fractionation column. At least 81 trays are located below the feed point and at least 31 trays are located above the feed point to this section of the column.

The net bottoms stream of the lower section of the column has a total flow rate of about 600 mph, of which approximately 555 mph is butene-2. The operating conditions at the top of this lower section of the column include a pressure of approximately 120 psig and a temperature of about 157° F. The vapor from the top tray of the lower section of the column is admixed with a recycle stream containing about 175 mph of hydrogen and heated to close to 212° F. This vapor admixture is then passed into a third reactor which functions as the second isomerization reaction zone. The effluent of this reactor is passed into the bottom of the upper section of the fractionation column, which contains an additional 23 trays. A liquid stream comprising the liquid descending from the lowest tray in the upper section of the column is withdrawn and fed to the top tray of the lower section of the column. This liquid stream has a flow rate of about 8000 mph and contains about 6030 mph isobutylene, 155 mph butene-1 and 1680 mph of butene-2. An overhead vapor stream containing approximately 195 mph of hydrogen is removed from the top of the upper section of the column and passed to the overhead condenser at a pressure of about 95 psig at a temperature near 136° F. in admixture with the stripping column overhead vapor. The partial condensation of this overhead vapor produces a liquid which is divided into a reflux stream of about 6,945 mph and a stripper feed stream of about 880 mph. The ten tray stripper basically removes hydrogen from the entering liquid to thereby produce a final product stream having a total flow rate of approximately 730 mph, of which about 680 mph is isobutylene.

I claim as my invention:

1. A hydrocarbon conversion process for the isomerization of acyclic olefinic hydrocarbons which comprises the steps of:
  (a) passing a feed stream comprising a first, a second and a third acyclic olefinic hydrocarbon, all of which have the same number of carbon atoms per molecule, through a first catalytic isomerization reaction zone maintained at isomerization conditions and thereby producing a first reaction zone effluent stream which has a higher concentration of the first olefinic hydrocarbon than the feed stream;
  (b) separating the first reaction zone effluent stream in a first fractionation zone into a first bottoms liquid stream having a higher concentration of the first olefinic hydrocarbon than the first reaction zone effluent stream and a first vapor stream having a higher concentration of the second olefinic hydrocarbon than the first reaction zone effluent stream and which is removed from an upper portion of the first fractionation zone;
  (c) passing the first vapor stream through a second catalytic isomerization reaction zone maintained at isomerization conditions and thereby producing a second reaction zone effluent stream which has a higher concentration of the first olefinic hydrocarbon than the first vapor stream;
  (d) separating the second reaction zone effluent stream in a second fractionation zone into a second bottoms liquid stream comprising the first olefinic hydrocarbon and a second vapor stream, which is rich in the third olefinic hydrocarbon;

(e) passing the second bottoms liquid stream into an upper portion of the first fractionation zone; and, (f) recovering a product stream which is rich in the third olefinic hydrocarbon from said vapor stream.

2. The process of claim 1 further characterized in that the second reaction zone effluent stream is passed into a lower portion of the second fractionation zone.

3. The process of claim 2 further characterized in that the second reaction zone effluent stream is a vapor-phase stream and is passed into the second fractionation zone as a vapor.

4. The process of claim 3 further characterized in that a vapor stream comprising hydrogen is admixed with the first vapor stream prior to the passage of the first vapor stream into the second reaction zone.

5. The process of claim 3 further characterized in that the first olefinic hydrocarbon is butene-2 and the third olefinic hydrocarbon is isobutylene.

6. A hydrocarbon conversion process which comprises the steps of:

(a) passing a feed stream comprising butene-1, butene-2 and isobutylene through a first catalytic isomerization reaction zone maintained at isomerization conditions and in which butene-1 is converted to butene-2 and thereby producing a first reaction zone effluent stream, which comprises butene-1, butene-2 and isobutylene;

(b) separating the first reaction zone effluent stream in a first fractionation zone into a first bottoms liquid stream, which is rich in butene-2, and a first overhead vapor stream comprising butene-1 and isobutylene;

(c) admixing a recycle vapor stream comprising hydrogen into the first overhead vapor stream;

(d) passing the first overhead vapor stream into a second catalytic isomerization zone maintained at isomerization conditions and in which butene-1 is converted to butene-2 and thereby producing a second reaction zone effluent stream which comprises butene-1, butene-2, isobutylene and hydrogen;

(e) separating the second reaction zone effluent stream in a second fractionation zone into a second bottoms liquid stream, which comprises butene-1 and butene-2, and a second overhead vapor stream, which comprises hydrogen and isobutylene;

(f) passing the second bottoms liquid stream into the first fractionation zone; and, (g) recovering a product stream comprising isobutylene from the second overhead vapor stream.

7. The process of claim 6 further characterized in that the recycle vapor stream comprises hydrogen recovered from the second overhead vapor stream.

8. The process of claim 6 further characterized in that the second bottoms liquid stream is passed into an uppermost section of the first fractionation zone and in that the second reaction zone effluent stream is passed into a lowermost section of the second fractionation zone.

9. The process of claim 8 further characterized in that the second reaction zone effluent stream is passed into the second fractionation zone as a vapor phase stream.

* * * * *